(12) United States Patent
Jack

(10) Patent No.: US 6,530,957 B1
(45) Date of Patent: Mar. 11, 2003

(54) MODULAR JOINT PROSTHESIS WITH MULTIPLE OFFSET HUMERAL HEAD COMPONENT AND METHOD

(75) Inventor: David A. Jack, Clifton, NJ (US)

(73) Assignee: Howmedica Osteonics Corp., Allendale, NJ (US)

(*) Notice: Subject to any disclaimer, the term of this patent is extended or adjusted under 35 U.S.C. 154(b) by 0 days.

(21) Appl. No.: 09/938,309

(22) Filed: Aug. 23, 2001

(51) Int. Cl.[7] .................................................. A61F 2/40
(52) U.S. Cl. .................................................. 623/19.14
(58) Field of Search ........................ 623/19.11–19.14, 623/17.11, 20.14, 22.11, 22.15, 22.43–22.45, 23.11, 23.15, 23.4

(56) References Cited

U.S. PATENT DOCUMENTS

| | | | |
|---|---|---|---|
| 4,865,605 A | | 9/1989 | Dines et al. |
| 5,156,624 A | * | 10/1992 | Barnes ..................... 623/22.45 |
| 5,282,865 A | | 2/1994 | Dong |
| 5,314,479 A | | 5/1994 | Rockwood, Jr. et al. |
| 5,358,526 A | | 10/1994 | Tornier |
| 5,405,403 A | * | 4/1995 | Mikhail ..................... 623/23.11 |
| 5,489,309 A | | 2/1996 | Lackey et al. |
| 5,507,817 A | | 4/1996 | Craig et al. |
| 5,549,682 A | | 8/1996 | Roy |
| 5,658,340 A | | 8/1997 | Muller et al. |
| 5,702,457 A | | 12/1997 | Walch et al. |
| 5,702,486 A | | 12/1997 | Craig et al. |
| 5,728,161 A | | 3/1998 | Camino et al. |
| 5,902,340 A | * | 5/1999 | White et al. ................. 128/898 |
| 5,910,171 A | | 6/1999 | Kummer et al. |
| 6,210,444 B1 | * | 4/2001 | Webster et al. .......... 623/20.33 |
| 6,228,120 B1 | * | 5/2001 | Leonard et al. .......... 623/19.12 |
| 6,364,910 B1 | * | 4/2002 | Shultz et al. ............. 623/19.13 |
| 2001/0053935 A1 | * | 12/2001 | Hartdegen et al. ....... 623/19.12 |

OTHER PUBLICATIONS

Tornier, Inc., Shoulder Prosthesis, Aequalis, undated.
Tornier, Inc., The Aequalis Shoulder Prosthesis, undated.

* cited by examiner

Primary Examiner—Kevin Shaver
Assistant Examiner—Michael B. Priddy
(74) Attorney, Agent, or Firm—Arthur Jacob

(57) ABSTRACT

A modular prosthesis, such as a shoulder prosthesis, enables the selection of one of multiple alternate offset locations of a head member, such as a humeral head member, on a stem member, such as a humeral stem member, together with the selection of any rotational orientation of the head member within a full 360° range of rotational orientation relative to the stem member, so as to locate and orient the head member secured on the stem member for optimum replication of the natural joint replaced by the prosthesis.

21 Claims, 3 Drawing Sheets

MODULAR JOINT PROSTHESIS WITH MULTIPLE OFFSET HUMERAL HEAD COMPONENT AND METHOD

The present invention relates generally to prosthetic implants and pertains, more specifically, to a modular joint prosthesis, such as a humeral shoulder prosthesis, and a method for implanting such a prosthesis in the natural bone to replace the natural head of a natural joint with a prosthetic implant.

It has been suggested that a humeral prosthesis of a prosthetic shoulder implant can be constructed in a modular fashion in which a prosthetic humeral head is included in a humeral head component selectively coupled, as by an interconnecting taper arrangement, with a humeral stem component. The advantages of such modular construction are described in several prior patents. Among those advantages is the ability to replicate the natural offset between the center of the humerus and the center of the humeral head by providing a connection arrangement for connecting the humeral head component to the humeral stem component with an appropriate offset. A modular construction enables the selection of a humeral head component which provides the desired offset when connected to the humeral stem component of the humeral prosthesis.

The present invention attains the above-outlined advantages of modular construction in a humeral shoulder prosthesis, and includes improvements which enable a surgeon to more readily and better fit the humeral shoulder prosthesis to the needs of a particular implant site so as to more accurately replicate the natural shoulder joint, and to do so interoperatively. In short, the present invention enables a single humeral head component to accommodate a wider range of offset requirements, thereby reducing the number of different humeral head components required to meet the needs of different implant sites. Further, the ability to provide a wider range of offset enables ready selection of a humeral head component for use in connection with implant sites which have experienced shoulder fractures and where it is desired to gain back arm length lost as a result of a foreshortened humerus ordinarily associated with a shoulder fracture.

Hence, the present invention attains several objects and advantages, some of which are summarized as follows: Provides a modular prosthesis, such as a modular shoulder prosthesis, and implant method enabling the accommodation of a wider range of offset requirements with a lesser number of sizes of component parts of the prosthesis; enables a more accurate accommodation of a particular offset requirement within the wider range of offset requirements; facilitates the choice and connection of a head component, such as a humeral head component of a shoulder prosthesis, to a stem component, such as a humeral stem component, with an accurate location and desired orientation of the humeral head component on the humeral stem component; allows the use of an appropriate offset provided by a humeral head component selected from a reduced number of sizes of humeral head components to gain back arm length lost as a result of a foreshortened humerus at the site of a shoulder fracture; reduces the requirement for larger inventories of component parts, with concomitant reductions in cost and increases in efficiency, as well as increases in economy of manufacture; provides a simplified construction in a humeral shoulder prosthesis for increased ease and accuracy in use, as well as increased ease of manufacture; provides a wider range of choices to a surgeon in accommodating the various conditions encountered at the implant site in different recipients of a humeral shoulder prosthesis; simplifies the implant procedure while enabling greater accuracy in effecting the implant; exhibits exemplary performance over a relatively long service life.

The above objects and advantages, as well as further objects and advantages, are attained by the present invention which may be described briefly as an improvement in a modular humeral shoulder prosthesis for implant in a natural humerus to replace a humeral head of a natural shoulder joint with a prosthetic implant which is to replicate the natural shoulder joint and in which a humeral head component is coupled with a humeral stem component in a prescribed location and orientation by the interoperative engagement of interlocking tapered connector elements located on the humeral head component and on the humeral stem component, the improvement comprising: a humeral head member including radius an obverse surface providing a bearing surface following a spherical surface contour having a prescribed radius and a central axis, and a reverse surface extending transverse to the central axis; a humeral stem member including a platform for confronting the reverse surface of the humeral head member, and a stem integral with and depending from the platform; multiple tapered connector elements including at least: a first tapered connector element located on the humeral head member and extending in a first direction spaced transversely from the central axis by a first predetermined offset distance; a second tapered connector element located on the humeral head member and extending in a second direction spaced transversely from the central axis by a second predetermined offset distance, the second predetermined offset distance being different from the first predetermined offset distance; and a third tapered connector element located on the humeral stem member and extending along a connector axis, the third tapered connector element being configured for selective interengagement with either one of the first and second tapered connector elements to secure the humeral head member to the humeral stem member, such that upon engagement of the third tapered connector element with a selected one of the first and second tapered connector elements, and subsequent seating of the humeral head member on the humeral stem member, with the humeral head member placed in a desired orientation about the connector axis and a desired offset location relative to the humeral stem member, the humeral head member is secured to the humeral stem member with the bearing surface placed for optimum replication of the natural shoulder joint.

In addition, the invention pertains to an improvement in a method for implanting a modular humeral shoulder prosthesis in a natural humerus to replace a humeral head of a natural shoulder joint with a prosthetic implant which is to replicate the natural shoulder joint and in which a humeral head component is coupled with a humeral stem component in a prescribed location and orientation by the interoperative engagement of interlocking tapered connector elements located on the humeral head component and on the humeral stem component, the improvement comprising: providing a humeral head member having an obverse surface including a bearing surface following a spherical surface contour having a prescribed radius and a central axis, and a reverse surface extending transverse to the central axis; providing a humeral stem member having a platform for engaging the reverse surface of the humeral head member, and a stem integral with and depending from the platform; providing multiple tapered connector elements including at least a first tapered connector element located on the humeral head member and extending in a first direction spaced transversely from the central axis by a first predetermined offset distance, a second tapered connector element located on the humeral head member and extending in a second direction spaced transversely from the central axis by a second predetermined offset distance, the second predetermined offset distance being different from the first predetermined offset distance, and a third tapered connector element located on the humeral stem member and extending along a connector axis, the third tapered connector element being configured for selective interengagement with either one of the first and second tapered connector elements to secure the humeral head member to the humeral stem member; engaging the third tapered connector element with a selected one of the first and second tapered connector elements, with the humeral head member placed in a desired orientation about the connector axis at a desired offset location relative to the humeral stem member; and subsequently seating the humeral head member on the humeral stem member, with the humeral head member placed in the desired orientation about the connector axis and at the desired offset location relative to the humeral stem member, to secure the humeral head member to the humeral stem member with the bearing surface placed for optimum replication of the natural shoulder joint.

In addition, the invention includes an improvement in a modular prosthesis for implant in a natural bone to replace a head of a natural joint with a prosthetic implant which is to replicate the natural joint and in which a head component is coupled with a stem component in a prescribed location and orientation by the interoperative engagement of interlocking tapered connector elements located on the head component and on the stem component, the improvement comprising: a head member including an obverse surface providing a bearing surface following a spherical surface contour having a prescribed radius and a central axis, and a reverse surface extending transverse to the central axis; a stem member including a platform for confronting the reverse surface of the head member, and a stem integral with and depending from the platform; and multiple tapered connector elements including at least: a first tapered connector element located on the head member and extending in a first direction spaced transversely from the central axis by a first predetermined offset distance; a second tapered connector element located on the head member and extending in a second direction spaced transversely from the central axis by a second predetermined offset distance, the second predetermined offset distance being different from the first predetermined offset distance; and a third tapered connector element located on the stem member and extending along a connector axis, the third tapered connector element being configured for selective interengagement with either one of the first and second tapered connector elements to secure the head member to the stem member, such that upon engagement of the third tapered connector element with a selected one of the first and second tapered connector elements, and subsequent seating of the head member on the stem member, with the head member placed in a desired orientation about the connector axis and a desired offset location relative to the stem member, the head member will be secured to the stem member with the bearing surface placed for optimum replication of the natural joint.

Further, the invention includes an improvement in a method for implanting a modular prosthesis in a natural bone to replace a head of a natural joint with a prosthetic implant which is to replicate the natural joint and in which a head component is coupled with a stem component in a prescribed location and orientation by the interoperative engagement of interlocking tapered connector elements located on the head component and on the stem component, the improvement comprising: providing a head member having an obverse surface including a bearing surface following a spherical surface contour having a prescribed radius and a central axis, and a reverse surface extending transverse to the central axis; providing a stem member having a platform for confronting the reverse surface of the head member, and a stem integral with and depending from the platform; providing multiple tapered connector elements including at least a first tapered connector element located on the head member and extending in a first direction spaced transversely from the central axis by a first predetermined offset distance, a second tapered connector element located on the head member and extending in a second direction spaced transversely from the central axis by a second predetermined offset distance, the second predetermined offset distance being different from the first predetermined offset distance, and a third tapered connector element located on the stem member and extending along a connector axis, the third tapered connector element being configured for selective interengagement with either one of the first and second tapered connector elements to secure the head member to the stem member; engaging the third tapered connector element with a selected one of the first and second tapered connector elements, with the head member placed in a desired orientation about the connector axis at a desired offset location relative to the stem member; and subsequently seating the head member on the stem member, with the head member placed in the desired orientation about the connector axis and at the desired offset location relative to the stem member, to secure the head member to the stem member with the bearing surface placed for optimum replication of the natural joint.

The invention will be understood more fully, while still further objects and advantages will become apparent, in the following detailed description of preferred embodiments of the invention illustrated in the accompanying drawing, in which.

Figure 1:
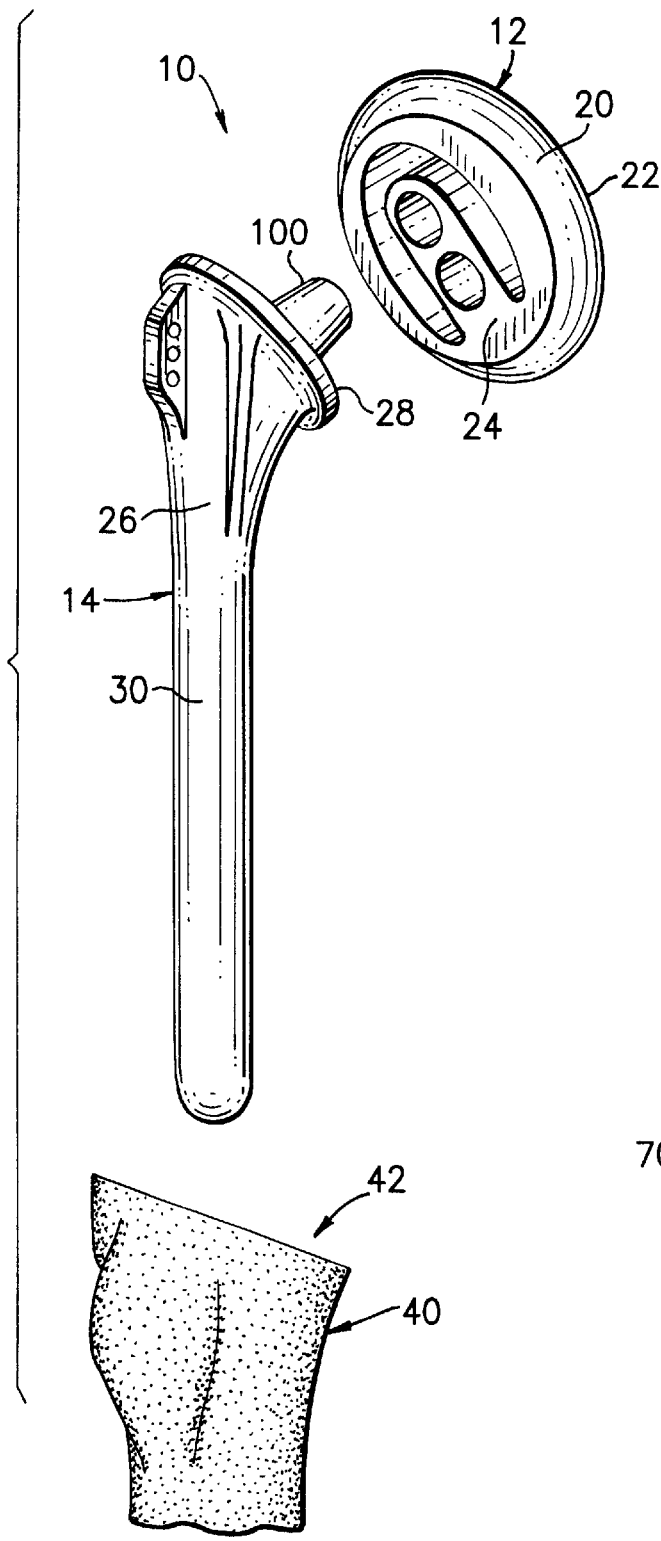
FIG. 1 is an exploded pictorial view of a modular prosthesis illustrated in the form of a humeral shoulder prosthesis constructed in accordance with the present invention, at an implant site.

Referring now to the drawing, and especially to FIG. 1 thereof, a modular prosthesis constructed in accordance with the present invention is illustrated generally at 10 and is shown in the form of a modular shoulder prosthesis having a humeral head component 12 and a humeral stem component 14. Humeral head component 12 includes a humeral head member 20 having a obverse surface 22 and a reverse surface 24. In the preferred construction, humeral head component 12 is in the form of a unitary structure constructed of a known bio-compatible material, such as a cobalt-chrome alloy. Humeral stem component 14 includes a humeral stem member 26 having a proximal platform 28 and an elongate stem 30 integral with and depending from the platform 28 to project downwardly for reception in a suitably prepared natural bone, shown as a natural humerus 40, in a predetermined position in the humerus 40, at an implant site 42. In the preferred construction, humeral stem component 14 is in the form of a unitary structure constructed of a known bio-compatible material, such as titanium or a cobalt-chrome alloy.

Figure 2:
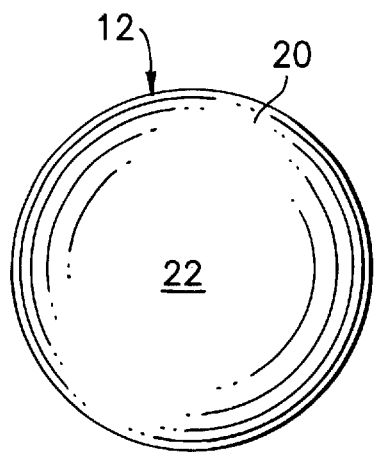
FIG. 2 is a front elevational view showing the obverse surface of the humeral head component of the prosthesis.
Figure 3:
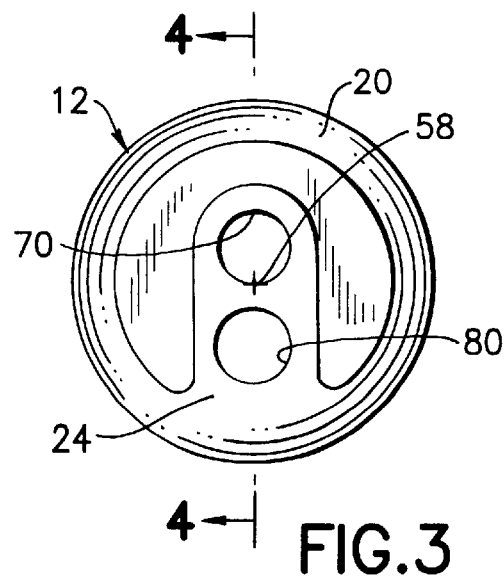
FIG. 3 is a rear elevational view showing the reverse surface of the humeral head component of the prosthesis.
Figure 4:
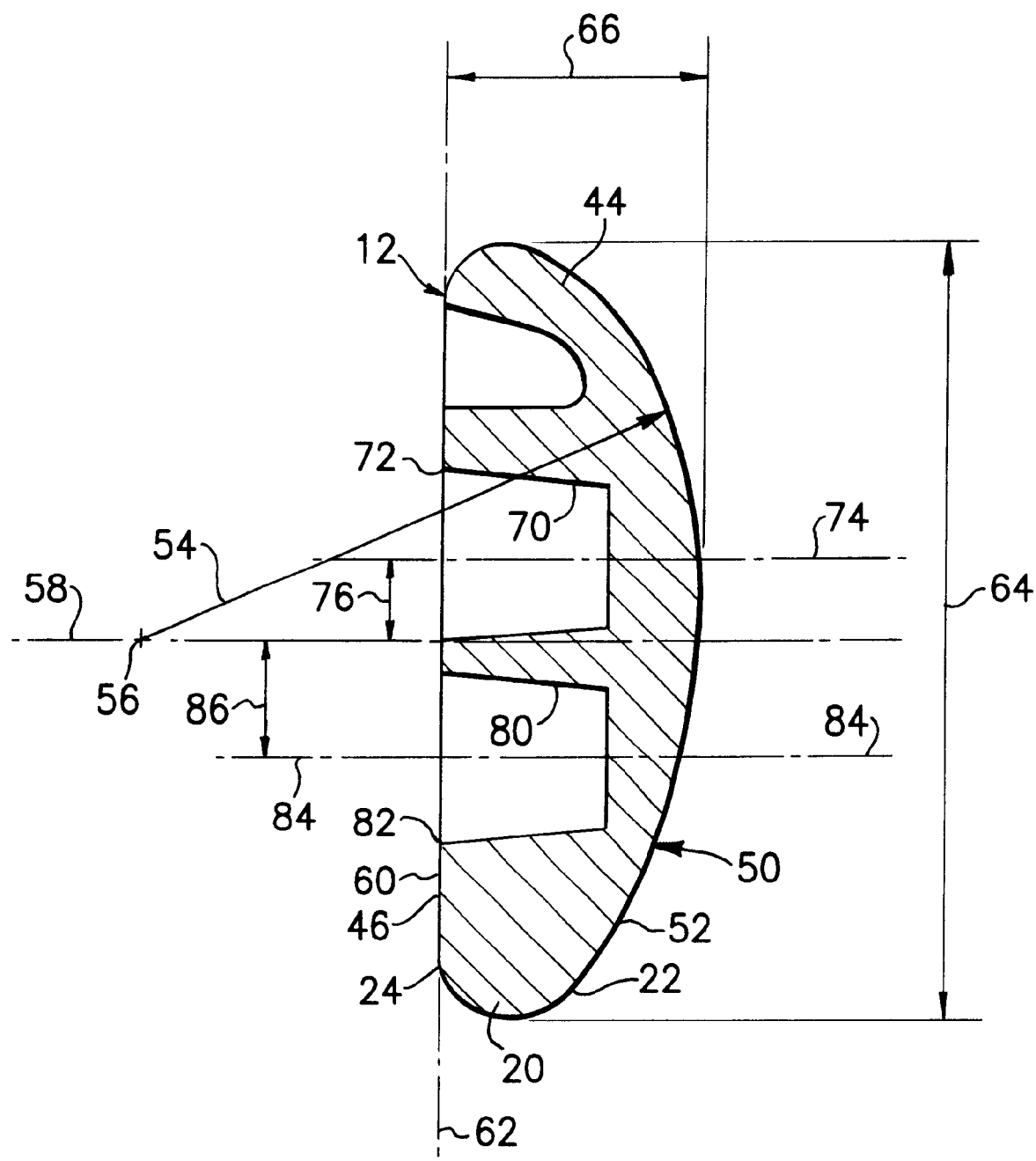
FIG. 4 is an enlarged cross-sectional view taken alone line 4—4 of FIG. 3.

Turning now to FIGS. 2 through 4, as well as to FIG. 1, the humeral head member 20 of humeral head component 12 is in the form of a generally spherical segment 44 having a base 46 at the reverse surface 24 and includes a bearing surface 50 at the obverse surface 22. The bearing surface 50 follows a spherical surface contour 52 having a predetermined radius 54 extending from an origin 56, and a central axis 58 passing through the origin 56. An undersurface 60 extends along the reverse surface 24, at the base 46 of the spherical segment 44, in a direction transverse to the central axis 58 and lies generally in a chordal plane 62 essentially normal to the central axis 58. The size of the humeral head member 20 is determined by the overall diameter 64 and the overall thickness 66 of humeral head member 20.

As best seen in FIG. 4, multiple tapered connector elements include at lease a first tapered connector element located on the humeral head member 20 and shown in the form of a first frustoconical bore 70 having an opening 72 at the undersurface 60 and extending into the humeral head member 20 from the reverse surface 24 toward the obverse surface 22, along a first direction 74 essentially parallel to central axis 58 and spaced transversely from the central axis 58 by a first predetermined offset distance 76, and a second tapered connector element located on the humeral head member 20 and shown in the form of a second frustoconical bore 80 having an opening 82 at the undersurface 60 and extending into the humeral head member 20 from the reverse surface 24 toward the obverse surface 22, along a second direction 84 essentially parallel to central axis 58 and spaced transversely from the central axis 58 by a second predetermined offset distance 86. In the preferred construction, the first direction 74 is located diametrically opposite the second direction 84, relative to the central axis 58 which lies between the first and second directions 74 and 84, with the first direction 74 essentially parallel to the second direction 84.

Figure 5:
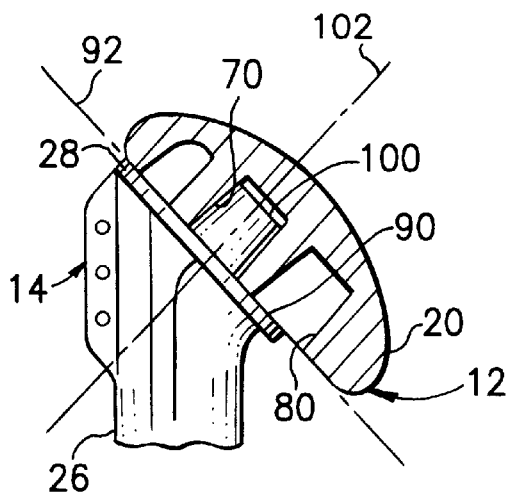
FIG. 5 is a fragmentary elevational view, partially cross-sectioned, showing the humeral head component secured to the humeral stem component of the humeral shoulder prosthesis in one selected location and orientation.
Figure 6:
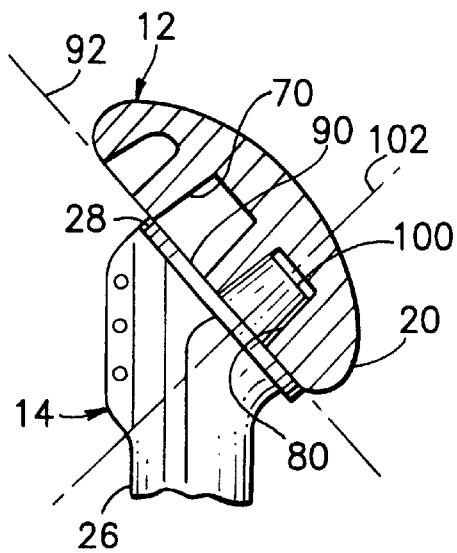
FIG. 6 is a fragmentary elevational view, partially cross-sectioned, showing the humeral head component secured to the humeral stem component of the humeral shoulder prosthesis in another selected location and orientation.

Turning now to FIGS. 5 and 6, as well as to FIG. 1, the platform 28 of the humeral stem member 26 includes an upper surface 90 which extends in a direction lying in a plane 92. The multiple tapered connector elements include a third tapered connector element located on the humeral stem member 26 and shown in the form of a frustoconical post 100 projecting generally upwardly from the platform 28 along a connector axis 102. The post 100 and the bores 70 and 80 are configured for selective interengagement of the post 100 with either one of the bores 70 and 80 to couple the humeral head member 20 with the humeral stem member 26. In the illustrated preferred configuration the post 100 and the bores 70 and 80 follow an interlocking Morse taper which serves to secure the humeral head member 20 on the humeral stem member 26 when the post 100 is coupled with either one of the bores 70 and 80 with the humeral head member 20 appropriately seated upon the humeral stem member 26, as shown.

The provision of multiple alternate bores 70 and 80 located at different offset distances 76 and 86, respectively, for selective coupling with post 100, enables a surgeon to place bearing surface 50 for optimum replication of the natural shoulder joint at the implant site 42, and to do so interoperatively. Thus, the tapered connector elements provide the ability to orient the humeral head member 20 in any selected orientation throughout a full 360° of rotation about the connector axis 102 and then secure the humeral head member 20 to the humeral stem member 26 at that selected orientation. The choice of offset distance offered by the alternate multiple offset distances 76 and 86, combined with the full 360° range of orientation, enables the accommodation of a wider range of conditions encountered at a particular implant site with a lesser number of sizes of humeral head members 20. For any one size of humeral head member 20, selection of lesser offset distance 76, as seen in FIG. 5, combined with the full 360° range of orientation, enables a more accurate accommodation to most conditions encountered at an implant site.

Where a particular condition at an implant site requires a greater adjustment, the selection of greater offset distance 86, as seen in FIG. 6, enables the accommodation of such a greater adjustment without requiring the availability of another humeral head member of another size. For example, at an implant site which has suffered a shoulder fracture resulting in a foreshortened humerus, a surgeon ordinarily will select a humeral head member of a size having a greater thickness in an effort to re-establish humeral head height so as to gain back arm length. Such a choice requires the availability of a greater number of humeral head members of different sizes. Moreover, the use of a thicker humeral head member to gain back arm length can result in "overstuffing" the shoulder joint, with concomitant undesirable effects. The availability of the greater offset distance 86 in humeral head member 20 enables the location and orientation of a suitably sized humeral head member for re-establishing head height and gaining back arm length without such deleterious effects. In humeral head member sizes ranging from 40 mm to 50 mm in diameter, and from 15 mm to 21 mm in thickness, the lesser offset distance 76 preferably is in the range of about 3 mm to 4 mm, while the greater offset distance 86 preferably is in the range of about 6 mm to 8 mm.

A surgical procedure conducted in accordance with the present invention includes selecting one of the bores 70 and 80 for engagement with the post 100 and then engaging the post 100 with the selected bore 70 or 80, with the humeral head member 20 placed in the desired orientation about the connector axis 102 and at a desired offset location relative to the humeral stem member 26. Subsequently, the humeral head member 20 is seated on the humeral stem member 26 to secure the members 20 and 26 together, with the reverse surface 24 of the humeral head member 20 confronting the platform 28 of the humeral stem member 26 and the bearing surface 50 placed for optimum replication of the natural shoulder joint.

Figure 7:
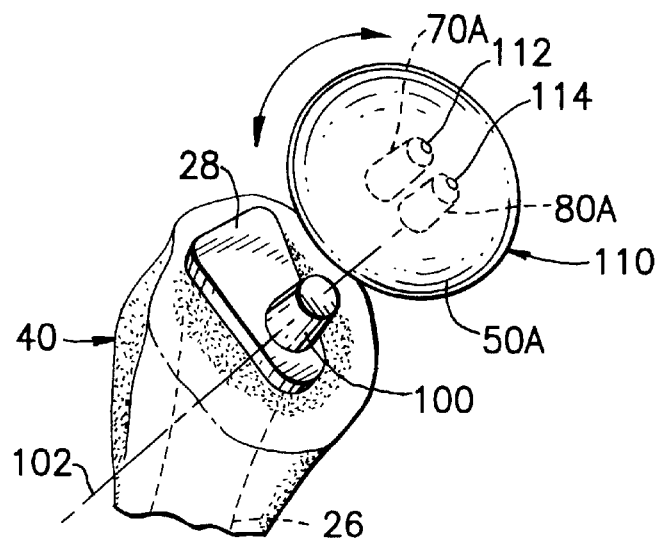
FIG. 7 is an exploded pictorial view showing a step in a surgical procedure for implanting the humeral shoulder prosthesis.

As depicted in FIG. 7, a humeral head trial member 110 is used to determine the proper diameter and thickness of the humeral head member to be implanted. The trial member 110 provides a simulated bearing surface 50A, includes bores 70A and 80A, corresponding to bores 70 and 80, and carries a first mark 112 visually indicating the offset location of selectable bore 70A, while a second mark 114 visually indicates the offset location of selectable bore 80A. A surgeon engages the trial member 110 with the post 100 of the humeral stem member 26, now implanted in the humerus 40, and rotates the trial member 110 about the connection axis 102 to determine the appropriate orientation. The combination of the selection of the appropriate bore 70A or 80A and the rotational orientation of the trial member 110 on the post 100 enables the surgeon to determine the appropriate offset location and the rotational orientation of the humeral head member 20 to be secured to the humeral stem member 26 at the implant site 42.

It will be seen that the present invention attains the several objects and advantages summarized above; namely: Provides a modular prosthesis, such as a modular shoulder prosthesis, and implant method enabling the accommodation of a wider range of offset requirements with a lesser number of sizes of component parts of the prosthesis; enables a more accurate accommodation of a particular offset requirement within the wider range of offset requirements; facilitates the choice and connection of a head component, such as a humeral head component of a shoulder prosthesis, to a stem component, such as a humeral stem component, with an accurate location and desired orientation of the humeral head component on the humeral stem component; allows the use of an appropriate offset provided by a humeral head component selected from a reduced number of sizes of humeral head components to gain back arm length lost as a result of a foreshortened humerus at the site of a shoulder fracture; reduces the requirement for larger inventories of component parts, with concomitant reductions in cost and increases in efficiency, as well as increases in economy of manufacture; provides a simplified construction in a humeral shoulder prosthesis for increased ease and accuracy in use, as well as increased ease of manufacture; provides a wider range of choices to a surgeon in accommodating the various conditions encountered at the implant site in different recipients of a humeral shoulder prosthesis; simplifies the implant procedure while enabling greater accuracy in effecting the implant; exhibits exemplary performance over a relatively long service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An improvement in a modular humeral shoulder prosthesis for implantation in a natural humerus to replace a humeral head of a natural shoulder joint with a prosthetic implant which is to replicate the natural shoulder joint and in which a humeral head component is coupled with a humeral stem component in a prescribed location and orientation by the interoperative engagement of interlocking tapered connector elements located on the humeral head component and on the humeral stem component, the improvement comprising:
   a humeral head member including an obverse surface providing a bearing surface following a spherical surface contour having a prescribed radius and a central axis, and a reverse surface extending transverse to the central axis;
   a humeral stem member including a platform for confronting the reverse surface of the humeral head member, and a stem integral with and depending from the platform; and
   multiple tapered connector elements including at least:
   a first tapered connector element located on the humeral head member and extending in a first direction spaced transversely from the central axis by a first predetermined offset distance;
   a second tapered connector element located on the humeral head member and extending in a second direction spaced transversely from the central axis by a second predetermined offset distance, the second predetermined offset distance being different from the first predetermined offset distance; and
   a third tapered connector element located on the humeral stem member and extending along a connector axis, the third tapered connector element being configured for selective interengagement with either one of the first and second tapered connector elements to secure the humeral head member to the humeral stem member, such that upon engagement of the third tapered connector element with a selected one of the first and second tapered connector elements, and subsequent seating of the humeral head member on the humeral stem member, with the humeral head member placed in a desired orientation about the connector axis and a desired offset location relative to the humeral stem member, the humeral head member will be secured to the humeral stem member with the bearing surface placed for optimum replication of the natural shoulder joint.

2. The invention of claim 1 wherein the first direction is located diametrically opposite the second direction, relative to the central axis.

3. The invention of claim 2 wherein the second predetermined offset distance is greater than the first predetermined offset distance.

4. The invention of claim 3 wherein the first offset distance is about 3 to 4 mm and the second offset distance is about 6 to 8 mm.

5. The invention of claim 1 wherein the first direction is essentially parallel to the second direction.

6. The invention of claim 5 wherein the first and second directions each are essentially parallel to the central axis.

7. The invention of claim 5 wherein the first and second tapered connector elements each comprise a frustoconical bore extending from the reverse surface into the humeral head member, and the third tapered connector element comprises a frustoconical post projecting from the platform of the humeral stem member along the connector axis.

8. The invention of claim 1 wherein the first and second tapered connector elements each comprise a frustoconical bore extending from the reverse surface into the humeral head member, and the third tapered connector element comprises a frustoconical post projecting from the platform of the humeral stem member along the connector axis.

9. The invention of claim 8 wherein the first direction is located diametrically opposite the second direction, relative to the central axis.

10. The invention of claim 9 wherein the frustoconical bores and the frustoconical post are configured such that the humeral head member is selectively secured to the humeral stem member in any selected orientation throughout a full 360° range of rotation of the humeral head member about the connector axis.

11. The invention of claim 8 wherein the frustoconical bores and the frustoconical post are configured such that the humeral head member is selectively secured to the humeral stem member in any selected orientation throughout a full 360° range of rotation of the humeral head member about the connector axis.

12. An improvement in a method for implanting a modular humeral shoulder prosthesis in a natural humerus to replace a humeral head of a natural shoulder joint with a prosthetic implant which is to replicate the natural shoulder joint and in which a humeral head component is coupled with a humeral stem component in a prescribed location and orientation by the interoperative engagement of interlocking tapered connector elements located on the humeral head component and on the humeral stem component, the improvement comprising:

providing a humeral head member having an obverse surface including a bearing surface following a spherical surface contour having a prescribed radius and a central axis, and a reverse surface extending transverse to the central axis;

providing a humeral stem member having a platform for confronting the reverse surface of the humeral head member, and a stem integral with and depending from the platform;

providing multiple tapered connector elements including at least a first tapered connector element located on the humeral head member and extending in a first direction spaced transversely from the central axis by a first predetermined offset distance, a second tapered connector element located on the humeral head member and extending in a second direction spaced transversely from the central axis by a second predetermined offset distance, the second predetermined offset distance being different from the first predetermined offset distance, and a third tapered connector element located on the humeral stem member and extending along a connector axis, the third tapered connector element being configured for selective interengagement with either one of the first and second tapered connector elements to secure the humeral head member to the humeral stem member;

engaging the third tapered connector element with a selected one of the first and second tapered connector elements, with the humeral head member placed in a desired orientation about the connector axis at a desired offset location relative to the humeral stem member; and subsequently seating the humeral head member on the humeral stem member, with the humeral head member placed in the desired orientation about the connector axis and at the desired offset location relative to the humeral stem member, to secure the humeral head member to the humeral stem member with the bearing surface placed for optimum replication of the natural shoulder joint.

13. The invention of claim 12 including securing the humeral head member to the humeral stem member in any selected orientation throughout a full 360° range of rotation of the humeral head member about the connector axis.

14. An improvement in a modular prosthesis for implantation in a natural bone to replace a head of a natural joint with a prosthetic implant which is to replicate the natural joint and in which a head component is coupled with a stem component in a prescribed location and orientation by the interoperative engagement of interlocking tapered connector elements located on the head component and on the stem component, the improvement comprising:

a head member including an obverse surface providing a bearing surface following a spherical surface contour having a prescribed radius and a central axis, and a reverse surface extending transverse to the central axis;

a stem member including a platform for confronting the reverse surface of the head member, and a stem integral with and depending from the platform; and multiple tapered connector elements including at least:

a first tapered connector element located on the head member and extending in a first direction spaced transversely from the central axis by a first predetermined offset distance;

a second tapered connector element located on the head member and extending in a second direction spaced transversely from the central axis by a second predetermined offset distance, the second predetermined offset distance being different from the first predetermined offset distance; and a third tapered connector element located on the stem member and extending along a connector axis, the third tapered connector element being configured for selective interengagement with either one of the first and second tapered connector elements to secure the head member to the stem member, such that upon engagement of the third tapered connector element with a selected one of the first and second tapered connector elements, and subsequent seating of the head member on the stem member, with the head member placed in a desired orientation about the connector axis and a desired offset location relative to the stem member, the head member will be secured to the stem member with the bearing surface placed for optimum replication of the natural joint.

15. The invention of claim 14 wherein the first direction is located diametrically opposite the second direction, relative to the central axis.

16. The invention of claim 14 wherein the first direction is essentially parallel to the second direction.

17. The invention of claim 16 wherein the first and second directions each are essentially parallel to the central axis.

18. The invention of claim 14 wherein the first and second tapered connector elements each comprise a frustoconical bore extending from the reverse surface into the humeral head member, and the third tapered connector element comprises a frustoconical post projecting from the platform of the humeral stem member along the connector axis.

19. The invention of claim 14 wherein the frustoconical bores and the frustoconical post are configured such that the humeral head member is selectively secured to the humeral stem member in any selected orientation throughout a full 360° range of rotation of the of the humeral head member about the connector axis.

20. An improvement in a method for implanting a modular prosthesis in a natural bone to replace a head of a natural joint with a prosthetic implant which is to replicate the natural joint and in which a head component is coupled with a stem component in a prescribed location and orientation by the interoperative engagement of interlocking tapered connector elements located on the head component and on the stem component, the improvement comprising:

providing a head member having an obverse surface including a bearing surface following a spherical surface contour having a prescribed radius and a central axis, and a reverse surface extending transverse to the central axis;

providing a stem member having a platform for confronting the reverse surface of the head member, and a stem integral with and depending from the platform;

providing multiple tapered connector elements including at least a first tapered connector element located on the head member and extending in a first direction spaced transversely from the central axis by a first predetermined offset distance, a second tapered connector element located on the head member and extending in a second direction spaced transversely from the central axis by a second predetermined offset distance, the second predetermined offset distance being different from the first predetermined offset distance, and a third tapered connector element located on the stem member and extending along a connector axis, the third tapered connector element being configured for selective interengagement with either one of the first and second tapered connector elements to secure the head member to the stem member;

engaging the third tapered connector element with a selected one of the first and second tapered connector elements, with the head member placed in a desired orientation about the connector axis at a desired offset location relative to the stem member; and subsequently seating the head member on the stem member, with the head member placed in the desired orientation about the connector axis and at the desired offset location relative to the stem member, to secure the head member to the stem member with the bearing surface placed for optimum replication of the natural joint.

21. The invention of claim 20 including securing the head member to the stem member in any selected orientation throughout a full 360° range of rotation of the head member about the connector axis.

* * * * *